United States Patent
Borgmeier et al.

(10) Patent No.: US 12,269,791 B2
(45) Date of Patent: Apr. 8, 2025

(54) PROCESS FOR THE PRODUCTION OF ANHYDROUS METHANESULFONIC ACID FROM METHANE AND SO3

(71) Applicant: BASF SE, Ludwigshafen am Rhein (DE)

(72) Inventors: Frieder Borgmeier, Ludwigshafen (DE); Frank Piepenbreier, Ludwigshafen (DE); Andreas Kempter, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 591 days.

(21) Appl. No.: 17/604,694

(22) PCT Filed: Apr. 14, 2020

(86) PCT No.: PCT/EP2020/060372
§ 371 (c)(1),
(2) Date: Oct. 18, 2021

(87) PCT Pub. No.: WO2020/212299
PCT Pub. Date: Oct. 22, 2020

(65) Prior Publication Data
US 2022/0194895 A1 Jun. 23, 2022

(30) Foreign Application Priority Data

Apr. 18, 2019 (EP) ..................................... 19170171
May 24, 2019 (EP) ..................................... 19176382

(51) Int. Cl.
*C07C 303/06* (2006.01)
*C07C 303/44* (2006.01)

(52) U.S. Cl.
CPC .......... *C07C 303/06* (2013.01); *C07C 303/44* (2013.01)

(58) Field of Classification Search
CPC .... C07C 303/06; C07C 303/44; C07C 309/04
See application file for complete search history.

(56) References Cited

U.S. PATENT DOCUMENTS

2006/0100458 A1   5/2006  Sen et al.
2018/0319739 A1*  11/2018 Spielmann ........... B01D 9/0045

FOREIGN PATENT DOCUMENTS

| CN | 1732141 A | 2/2006 |
|---|---|---|
| CN | 105722819 A | 6/2016 |
| CN | 108602766 A | 9/2018 |
| WO | 2004/041399 A2 | 5/2004 |
| WO | WO2004/041399 * | 5/2004 |
| WO | 2007/136425 A2 | 11/2007 |
| WO | 2015/071455 A1 | 5/2015 |
| WO | WO2017/080991 * | 5/2017 |
| WO | 2018/096138 A1 | 5/2018 |
| WO | 2018/146153 A1 | 8/2018 |
| WO | 2018/208701 A1 | 11/2018 |
| WO | WO2018/208701 * | 11/2018 |
| WO | 2018/219726 A1 | 12/2018 |

OTHER PUBLICATIONS

European Search Report for EP Patent Application No. 19170171.3, Issued on Oct. 11, 2019, 3 pages.
European Search Report for EP Patent Application No. 19176382.0, Issued on Oct. 10, 2019, 3 pages.
International Search Report for PCT Patent Application No. PCT/EP2020/060372, Issued on Jun. 30, 2020, 4 pages.
Kappenthuler, et al., "Environmental assessment of alternative methanesulfonic acid production using direct activation of methane", Journal of Cleaner Production, vol. 202, Nov. 20, 2018, pp. 1179-1191.
Lobree, et al., "K2S2O8-Initiated Sulfonation of Methane to Methanesulfonic Acid", Industrial & Engineering Chemistry Research, vol. 40, Issue 3, Jan. 6, 2001, pp. 736-742.

* cited by examiner

*Primary Examiner* — Yevgeny Valenrod
*Assistant Examiner* — Blaine G Doletski
(74) *Attorney, Agent, or Firm* — ArentFox Schiff LLP

(57) ABSTRACT

The present invention relates to a process for manufacturing of anhydrous methanesulfonic acid (MSA) and to methanesulfonic acid manufactured by said process and its uses.

26 Claims, 2 Drawing Sheets

PROCESS FOR THE PRODUCTION OF ANHYDROUS METHANESULFONIC ACID FROM METHANE AND SO3

CROSS-REFERENCE TO RELATED APPLICATIONS

This application is a National Stage Entry of PCT/EP2020/060372, filed Apr. 14, 2020, which claims priority to EP application No. 19170171.3, filed Apr. 18, 2019, and EP application No. 19176382.0, filed May 24, 2019, the disclosures of each of which are hereby incorporated by reference in their entireties.

The present invention relates to a process for manufacturing of anhydrous methanesulfonic acid (MSA) and to methanesulfonic acid manufactured by said process and its uses.

Methanesulfonic acid ($H_3CSO_3H$, MSA), like other alkanesulfonic acids, is a strong organic acid which is used for a multiplicity of different processes, for example for electroplating processes, in chemical processes or in cleaning applications, or for example in semiconductor industry or as rust and scale remover.

A high purity of methanesulfonic is key for many applications. At the same time energy demand, environmental impact and investment cost should be as low as possible to provide a cost competitive process.

A recent and very promising approach describes the production of MSA by reacting methane and SO3 (e.g. WO 2004/041399, WO 2015/071455). Published data show that in the course of the synthesis a number of side products form which increases the effort to purify anhydrous MSA and consequently renders such a process inefficient and expensive.

WO 2004/041399 describes a method for converting methane into an oxygenated derivative, e.g. into MSA. The synthesis of MSA is achieved in high yields. With regard to the selectivity of the reaction it is stated that "the process only generates very small quantities of byproducts" and "in most cases MSA was the only product that was found in the liquid phase".

In the example section it is stated that the samples were analyzed by 1H NMR (liquid product) and by gas chromatography. Prior to analysis the liquid reaction product was diluted with water. No results of the NMR or the GC analysis are given beyond the information that no carbon dioxide was detected in the gas phase. WO 2004/041399 gives no indication on how to purify MSA. The absence of any significant amounts of byproduct after the synthesis is also emphasized by the same author when using dimethylsulfonylperoxyde (DMSP) as radical starter in WO 2007/136425. The only potential byproduct mentioned is sulfuric acid, but its amount is nowhere quantified. Again, no indication is given on the purification of MSA.

WO 2015/071455 describes an alkylsulfonylperoxide compound, which is used as radical starter in the production of MSA from methane and SO3, and a process to produce an alkanesulfonic acid from an alkane and SO3, especially MSA from methane and SO3, by using this initiator. It is mentioned that purification of the raw product can be processed e.g. by extraction, crystallization, distillation or chromatography. A preferred method to purify the raw MSA is distillation. However, no information is given on how the reaction mixture is delivered to the distillation, how such a distillation set-up may look like and which operational conditions could be applied.

WO 2018/146153 from the same applicant describes the same reaction, but again no information is given if any byproducts formed and if so in which concentration. Purification of the raw MSA is proposed by distillation, but no information is given on how the reaction mixture is delivered to the distillation, how such a distillation set-up may look like and which operational conditions could be applied.

In his article "Environmental assessment of alternative MSA production using direct activation of methane" (Journal of Cleaner Production, 202 (2018), pp. 1179-1191), S. Kappenthuler et al. describe that, after release of the synthesis pressure, excess SO3 is treated with water to create sulfuric acid prior to the distillation. The distillation yields MSA (99.5% pure) and a mixture of sulfuric acid and MSA with an 80/20 ratio. However, the publication provides no further information on side products, purification set-up and operational conditions.

WO 2018/208701 claims a process for recovering anhydrous methanesulfonic acid, in a purified form, from a feed stream comprised of hydrocarbon, methanesulfonic acid and SO3. Key step of this process is first to release the pressure of the synthesis, and then to contact the feed stream to the distillation with a reactive additive capable of reacting with SO3 to remove SO3 from the feed stream prior to the distillation and convert it to a reaction product having a boiling point higher than the boiling point of sulfur trioxide. If water is the reactive additive, sulfuric acid is being formed. There is no indication or hint in said publication to reverse the order of reaction or purification steps.

Even though the addition of a reactive additive simplifies the distillation, it requires a significant effort to separate methane, which evolves in gaseous form from the synthesis mixture after release of the pressure, from acidic compounds, namely SO3, e.g. in a scrubbing tower using a solution of caustic for scrubbing.

Potential byproducts from the reaction of methane and SO3 using Marshalls acid as starter are described in US 2006/0100458. The authors achieve selectivities to MSA in the liquid of over 99% with less than 1% of the following components combined: CH3OS(O2)OH (Methylbisulfate), (CH3O)2SO2 (Dimethylsulfate), CH3S(O2)OCH3 (Methylmethanesulfonate), and CH2(S(O2)OH)2 (Methanedisulfonic acid).

For the purification step by distillation of MSA, which is formed by the reaction of methane and SO3 using a mixture containing Marshall's acid as starter, WO 2018/219726 describes the formation of the following byproducts in the distillation process: CH2(S(O2)OH)2 (Methanedisulfonic acid), CH3OS(O2)OH (Methylbisulfate), and CH3S(O2)OCH3 (Methylmethanesulfonate). Moreover, the feed stream to the distillation in the examples comprises CH3S(O2)O(O2)SCH3 (Methanesulfonic acid anhydride), which might form by reaction of MSA and SO3 in the synthesis step yielding MSA anhydride and sulfuric acid.

SO3 in the presence of MSA supports the formation of side product at higher temperatures, e.g. Methylbisulfite, MSAA etc.

Consequently, there is a strong need for an improved process to provide anhydrous MSA from compositions comprising SO3 in an effective way with high purity.

Surprisingly, the inventors have now found a process which overcomes the deficiencies of the prior art and solves at least some of the above problems.

The invention thus, inter alia, relates to a process to provide anhydrous MSA from compositions comprising SO3 in an effective way with high purity.

One object of the present invention therefore is a process to provide anhydrous methanesulfonic acid (MSA), preferably with high purity, from compositions comprising SO3 which includes a reaction set-up comprising the following steps A. generating a first MSA stream ("stream A") which, apart from MSA, still comprises SO3 and methane under pressure;
B. adding to this MSA stream under pressure, e.g. by mixing, a reactive agent which is capable of reacting with SO3, under conditions effective to cause reaction of SO3 with this reactive agent to produce a heavy reaction product having a boiling point higher than the boiling point of MSA, thus generating a stream B;
C. separating this stream to provide a light stream comprising hydrocarbons and a heavy stream comprising MSA and a heavy reaction product having a boiling point higher than the boiling point of MSA;
D. and D. separating the heavy stream by distillation to produce a distillate stream consisting essentially of MSA and a bottoms stream comprising the heavy product.

In the context of the present invention, instead of methanesulfonic acid (MSA), other alkanesulfonic acids, like for example ethanesulfonic acid, may be used, alone or in combination with methanesulfonic acid.

For the sake of clarity, it should furthermore be mentioned that in the inventive process steps A to D are performed in the sequence indicated by the letters, i. e. first step A is conducted, then step B, then step C, followed by step D.

Thus, one aspect of the invention provides a process which includes a reaction set-up A. generating a first MSA stream ("stream A") which, apart from MSA, still comprises SO3 and methane under pressure;
B. adding to this MSA stream under pressure, e.g. by mixing, a reactive agent which is capable of reacting with SO3, under conditions effective to cause reaction of SO3 with this reactive agent to produce a heavy reaction product having a boiling point higher than the boiling point of MSA, thus generating a stream B;
C. separating this stream to provide a light stream comprising hydrocarbons and a heavy stream comprising MSA and a heavy reaction product having a boiling point higher than the boiling point of MSA;
D. and separating the heavy stream by distillation to produce a distillate stream consisting essentially of MSA and a bottoms stream comprising the heavy product.

This process has the advantage that the light stream comprising hydrocarbons generated in step C is basically free of SO3 and thus allows straight use of the hydrocarbons for various purposes, e.g. to generate energy by incineration, or to recycle the hydrocarbons to the process with significantly reduced purification efforts, or even making purification of the stream comprising hydrocarbons for further use completely obsolete. At the same time this way of conducting the process for the manufacture of anhydrous MSA reduces the risk of side reactions of SO3 in the distillation step D, simplifies the complexity of the distillation and reduces if not totally eliminates the amount of SO3 slipping through the distillation without being separated from the final product anhydrous MSA.

Thus, the process of the invention yields a very effective way to produce MSA with high purity and at the same time allows to significantly reduce the effort—if not the necessity at all—of additional purification steps for streams generated in the course of the process.

Further aspects of the invention comprise the following:

Stream A may be generated in a process consisting of at least
i. a step to produce an initiator for the reaction of SO3 and methane,
ii. a step to react SO3 and methane in the presence of the initiator generated in the previous step i.—optionally in a solvent containing MSA and/or sulfuric acid and/or a recycle stream from the bottom of the distillation column or set of columns in step D.

Stream A therefore contains MSA, unreacted methane and unreacted SO3. Moreover, it may contain one or more compounds selected from the list of sulfuric acid, methanesulfonic acid anhydride (MSAA), methylmethanesulfonate (MMS), methylbisulfite, unreacted or modified initiator (i.e. peroxides), polysulfuric acid etc. Stream A is typically generated in a reactor or a reactor cascade operated at a temperature between 0° C. and 130° C. and a pressure between 20 and 150 bar.

In a preferred embodiment, the temperatures to generate stream A in a reactor or a reactor cascade are between 20° C. and 90° C., and most preferred between 30° C. and 70° C., or any temperatures in between.

In a preferred embodiment, the pressures to generate stream A in a reactor or a reactor cascade are between 40 and 120 bar, most preferred between 50 and 100 bar.

The initiator may be synthesized by reaction of sulfuric acid or oleum or MSA or mixtures thereof with an aqueous solution of hydrogenperoxide. Optionally this mixture may contain MSAA as water scavenger and/or a recycle stream from the distillation in step D. Optionally a solution of hydrogen peroxide could be used as starter directly and be dosed to step ii. or into one of the feed streams to step ii, e.g. into SO3 or into the recycle stream from distillation (step D). The initiator is typically synthesized at temperatures between −5° C. and 50° C., preferred between 0° C. and 30° C., especially preferred between 3° C. and 20° C. The pressure at the synthesis of the starter is typically between 0.8 and 100 bara, preferred between 0.9 and 50 bara or 0.9 and 20 bara. The pressure can also be in the range of normal pressure (ca. 1 bara).

Methane can be in pure form if available. Primary sources of methane may be natural gas, LNG, biogas, steam cracker etc. However, these sources normally suffer from a methane purity which is not suitable for the inventive process. In such a case methane needs to be purified, e.g. by means of a pressure swing absorption unit or other techniques described in the literature. Typical impurities of methane, depending on its source, comprise higher saturated or unsaturated hydrocarbons, both linear and branched, e.g. ethane, propane, i-butane, ethylene etc. Other potential impurities comprise CO, CO2, hydrogen, nitrogen, noble gases, e.g. argon, hydrogensulfide etc.

SO3 may be introduced into the process taken from oleum as SO3 carrier or it may be taken in its pure form, e.g. condensed from the stream of a classical SO3 or sulfuric acid generation unit. If oleum is used as SO3 source, it is advantageous to distill pure SO3 out of the oleum leaving a partially depleted oleum with a lower SO3 concentration. If adding oleum itself to the reaction the content of sulfuric acid in the process increases and this additional sulfuric acid adds to the purge volume which needs to be treated when leaving the process, e.g. by neutralization. When oleum is used the depleted oleum is normally sent back to a sulfuric acid or oleum generation unit and the SO3 content of the oleum is increased again. In this sense oleum undergoes a cycle of SO3 depletion and SO3 enrichment. Depending on its source SO3 may still contain impurities such as SO2, oxygen, nitrogen, CO2 and others. The content of these impurities should be less than 5%, preferred less than 3%, less than 2%, less than 1% or 0.5% or 0.1%.

The SO3 may not be present as such. If SO3 and sulfuric acid are present in a solution, they immediately react with each other forming disulfuric acid. Thus, under conditions which enable the formation of alkane sulfonic acid, e. g. methanesulfonic acid, from alkane (hydrocarbon), e. g. methane, and SO3, free SO3 will hardly be present in a reaction mixture, but it will always be present in the form of disulfuric acid or a corresponding alkyl disulfuric acid, for example $CH_3$—$SO_2$—O—$SO_3H$. If in the following disulfuric acid is mentioned, this always also means the corresponding alkyl disulfuric acid. In the presence of water, however, disulfuric acid reacts with water to sulfuric acid (e.g. in step B).

In one embodiment, the method of producing the alkane sulfonic acid (in particular methanesulfonic acid) being the basis for providing a reaction mixture in step A is a method as disclosed in WO 2018/096138 A1. Thus, in a first step the alkane sulfonic acid (e. g. methanesulfonic acid) and hydrogen peroxide are reacted with each other to form a compound according to the following formula (I)

ALK-SO$_2$—O—O—X     (I)

wherein ALK is a branched or unbranched alkyl group, especially a methyl, ethyl, propyl, butyl, isopropyl, isobutyl group, or a higher alkyl group, wherein the alkyl group may optionally be halogenated, and X=hydrogen, zinc, aluminium, an alkali or alkaline earth metal. This compound according to formula (I) is then provided in a reactor together with sulfur trioxide and the alkane. Due to the addition of the alkane (in particular methane), pressure within a range of from 1-200 bar, preferably between 40 and 120 bar, is set. The reaction mixture is inside a high-pressure reactor and the temperature is controlled to be within a range of from 0° C. to 100° C., preferably between 0° C. and 30° C.

Step B

In one aspect the reactive agent added in step B not only reacts with SO3 but also converts hydrolysable compounds in this stream to further reduce the complexity of stream B for work-up as described in steps C and D.

In one embodiment the reactive additive can be a liquid or a gaseous compound or mixture of compounds.

In one embodiment the reactive additive is water and the heavy reaction product having a boiling point higher than the boiling point of MSA is sulfuric acid. Hydrolysable compounds reacting with water comprise e.g. MSAA (being converted to two moles of MSA upon reaction with water), MMS (being converted to one mole of MSA and one mole of methanol), polysulfuric acid, as e.g. disulfuric acid (being converted to sulfuric acid) etc.

In one embodiment the reactive additive is added in an amount understochiometric, stochiometric or overstochiometric regarding the molar amount of SO3 in stream A. Adding the reactive agent in equimolar amounts or with molar excess regarding SO3 is preferred. The molar excess may be +2% on a molar basis relative to SO3 in stream A, or +5%, +10%, +20%, +50%, +100% or above 100% on a molar basis relative to SO3 in stream A. Stochiometric addition of water relative to the molar amount of SO3 in stream A or a small access is most preferred.

In one embodiment the reactive additive is added in an amount understochiometric, stochiometric or overstochiometric regarding the total molar amount of SO3 and hydrolysable compounds in stream A. Adding the reactive agent in stochiometric amounts or with molar excess regarding the total molar amount of SO3 and hydrolysable compounds in stream A is preferred. The molar excess may be +2% on a molar basis relative to the total of SO3 and hydrolysable compounds in stream A, or +5%, +10%, +20%, +50%, +100% or above 100% on a molar basis relative to the total of SO3 and hydrolysable compounds in stream A. Stochiometric addition of water relative to the total molar amount of SO3 and hydrolysable compounds in stream A or a small access is most preferred.

In one embodiment, if water is used as reactive agent, the water needs to have a sufficient purity for the process so that no new impurities are introduced into the process which would be intolerable for process operation or product quality. Water with a sufficient purity may for example be demineralized water, drinking water, steam condensate, etc.

In one embodiment, the reactive agent is at least one compound selected from the group of alcohols, ethers, alkylbenzenes and alpha olefins.

In one embodiment the addition of the reactive agent in step B is realized by mixing the reactive agent into the process stream using a suitable set-up like a static mixture, a simple connection of two pipelines, a dedicated vessel (with or without stirrer), a mixer drum, a nozzle, a jet nozzle, a heat exchanger or any other means suitable for thorough mixing. The mixing may be a fast or a slow process.

In one embodiment, step B can be carried out at the same temperature at which the stream leaves step A, or at a higher temperature or at a lower temperature. By addition of the reactive agent to steam A it is expected that the temperature changes. This is acceptable for the process, both for step B itself and for the following steps C and D. Optionally this temperature change can be compensated for by removing or adding energy, e.g. by selecting a suitable temperature of the reactive agent prior to addition, or by introducing a heat exchanger, or a combination thereof. For example, when water is used as reactive agent, it is accepted that the temperature increases during step B due to the heat of reaction of water and SO3. A temperature increase is even helpful as it facilitates separation in steps C and D.

In one embodiment, the addition of the reactive agent can be done in a fixed amount, e.g. derived from an overall mass balance. For example, the amount of additive which is added in step B of the present application can be calculated depending on the amount of disulfuric acid being present in the reaction mixture, or based on the amount of SO3 used as raw material corrected by the amount of SO3 converted in the course of the reaction thus yielding the amount of free SO3.

Alternatively, the addition of the reactive agent can be controlled by means of an offline or an inline process analytics. Offline analytics, e.g. based on a daily or weekly sampling, allows to adjust the amount of reactive agent added in step B on a daily or weekly basis, which may be acceptable if the process runs very stable and with no or very few load changes. Inline analytics, e.g. based on spectroscopic techniques, on conductivity measurements, on titration, on chromatographic or other techniques, allows to adjust the amount of reactive agent added in step B in much shorter intervals depending on the time scale of the respective analytical technique. Normally this is beneficial for process control, i.e. to minimize overdosing or avoid underdosing of the reactive agent. Therefore it is preferred to apply a suitable method for inline analytics in step B.

Step C

The separation of stream B to provide a light stream comprising hydrocarbons and a heavy stream comprising MSA and sulfuric acid may be realized by reducing the pressure to normal pressure, to a pressure above normal pressure or below normal pressure. Reducing the pressure to the range of normal pressure is preferred, i.e. to a pressure in the range of 0.5 to 5 bara, more preferred 0.8 bara to 3 bara or 0.9 bara to 1.5 bara.

In one embodiment separating the hydrocarbons from the mixture may for example be done by simply reducing the pressure in a reactor so that the hydrocarbon can exhaust. For example, when operating the process in batch mode, steps B and C could be carried out in one reactor, e.g. the same reactor which is used for step A.

In one embodiment it would also be possible to remove only the liquid phase from a reactor so that the gas phase comprising the hydrocarbons remains in the reactor. For example, when operating the process in conti mode, only the liquid phase still containing small amounts of hydrocarbons could be removed from the reactor or set of reactors in step A (the largest portion of the hydrocarbon remaining in the reactor as gas phase), undergo treatment as described in step B and then carry out step C.

In one embodiment, reduction of the pressure may be done in one step or in multiple steps, at a temperature which the stream originally has after leaving step B, or at a higher or a lower temperature. Pressure reduction by expansion of the hydrocarbons and other potential light boilers in steam C may cool down stream C in the process of expansion. This cooling effect during expansion may be compensated for, e.g. by heating with a heat exchanger, if deemed necessary.

In one embodiment, step C may be carried out in a gas-liquid separator or a set of gas-liquid separators, in a vessel or a set of vessels, in a column or a set of columns, in a single flash or in multiple flashing steps each step reducing the pressure compared to the previous step. If a series of equipment is used, this equipment is operated in a way that the pressure of step n+1 is always lower than the pressure in step n. If a series of equipment is used each individual equipment may be operated at the same temperature or at different temperatures.

In one embodiment, a further step C* is introduced in which stream C after decompression, i.e. after the light boilers comprising methane were removed, is heated prior to entering the distillation step D. Heating is done to a temperature which is in the range between the outlet temperature at step C and the operation temperature of the first column or set of columns of step D.

The light stream typically comprises methane and other hydrocarbons introduced via the raw material methane or generated in the course of the process.

The heavy stream comprises, apart from MSA and sulfuric acid as mentioned above, other high boilers like for example methanedicarbonic acid or polysulfuric acid.

If no water is added in step B to capture SO3 and optionally hydrolyse hydrolysable compounds, light boilers, especially methane, leaving stream B after decompression require scrubbing prior to further handling, e.g. by scrubbing with sulfuric acid or a solution of caustic or other agents. This increases the equipment needed for such a process, the consumption of chemicals and the energy consumption of such a process. Therefore, it is key to simplify the process and operate it in an effective way as suggested in the present invention.

Step D

In a last step, the remaining reaction mixture comprising the alkane sulfuric acid (in particular methane sulfonic acid) as well as sulfuric acid can be distilled. The distillation can be performed in one or more distillation columns. Preferably, it is performed in at least two distillation columns. The use of several distillation columns enables the higher purity of the obtained alkane sulfonic acid. Residues of sulfuric acid or any other side product can be separated. In principle, it is possible by defining the parameters of distillation, namely the number of steps in the column, pressure and temperature inside the column etc. to define the purity of the alkane sulfonic acid (in particular methanesulfonic acid) and to adapt the amount impurities, especially sulfuric acid and SO3.

The distillation of step D can be realized in one column or a set of columns where each column has a different function. Each column with a different function can be realized as one column or as a set of columns operated in parallel depending on the target capacity and potential constraints regarding the size of the respective equipment. Suitable set-ups for the distillation to obtain anhydrous and pure MSA are described e.g. in WO 2018/219726.

In one embodiment, this distillation step generates anhydrous MSA with a purity of more than 98 wt-% MSA or more than 99 wt-% MSA. In a well selected set-up MSA purity can even be more than 99.5 wt-% MSA or 99.8 wt-% MSA. Typical MSA specifications established in the market today indicate a purity of 99.5 wt-% MSA or more.

In one embodiment, the content of SO3 in the MSA leaving the distillation step D is below 200 ppm, or below 100 ppm, or below 50 ppm. The SO3 content in the MSA leaving step D can even be as low as 30 ppm or 20 ppm or 10 ppm or 5 ppm. Purified MSA leaving step D can even be completely free of SO3.

In one embodiment, the content of sulfuric acid or equivalents thereof (e.g. sulfate) in the MSA leaving the distillation step D is below 500 ppm, or below 300 ppm, or below 200 ppm. The content of sulfuric acid or equivalents thereof in the MSA leaving step D can be as low as 100 ppm or 70 ppm or 50 ppm or 30 ppm. Purified MSA leaving step D can even contain sulfuric acid or equivalents thereof to an amount below 20 ppm or below 10 ppm or 5 ppm.

In one embodiment, the purified anhydrous MSA leaving the distillation step D still contains a total of compounds other than MSA ("impurities") below 5000 ppm, or below 4000 ppm, 3000 ppm, 2000 ppm, 1000 ppm, 800 ppm, or below 600 ppm. The amount of impurities in the MSA leaving step D may even be lower than 500 ppm or 200 ppm or 100 ppm.

The term "anhydrous" MSA in this context is used as it is established in the MSA market today, meaning that anhydrous translates into a water content of less than 0.5 wt-%, or less than 0.4 wt-%, or less than 0.3 or 0.2 wt-% or 0.1 wt-% of water. Water is no significant part of the process, but it may be introduced during synthesis of the initiator, e.g. when using an aqueous solution of hydrogen peroxide, or it may be introduced in step B of the inventive process.

The stream leaving the distillation column or set of columns at the bottom consists of high boilers, mainly of sulfuric acid and MSA. Moreover it may contain other high boilers as methanedisulfonic acid, polysulfuric acid etc.

In one embodiment, this high boiler stream may be completely purged, or some part may be purged and another part recycled into the process. If some part of this stream is recycled it may be fed into step A, more precisely to the synthesis of the initiator and/or to the reaction between methane and SO3.

Distillation is realized at temperatures between 130° C. and 220° C. at the bottom of the column or set of columns, preferred between 160° C. and 200° C. The pressure in the distillation at the head of the column or each individual column in a set of columns is typically between 0.1 mbara and 100 mbara, preferred between 1 mbara and 50 mbara, and most preferred between 2 mbara and 20 mbara or 15 mbara.

In general, cooling of equipment or process streams in the suggested process, steps A to D, is done using air or water, e.g. river water, demineralized water, cold water meaning water cooled down in a cold unit to e.g. 5° C. etc., or mixtures of water-glycol as cooling liquid. The cooling can be done using the primary source of cooling agent. In some cases, however, it might be of advantage to set up a closed system providing secondary cooling to the process. Such a secondary cooling system would be cooled via a central heat exchanger by the primary cooling agent. All cooling agents listed above could be used for such secondary cooling.

In general heating of equipment and process streams in the suggested process, steps A to D, is done using steam or heating oil or heated air or other agents typically used for such purposes.

A further object of the present invention is also anhydrous methanesulfonic acid (MSA), obtainable by the inventive process.

Schematic illustrations of potential process set-ups are shown in FIGS. 1 to 3.

EXAMPLES

Figure 1:
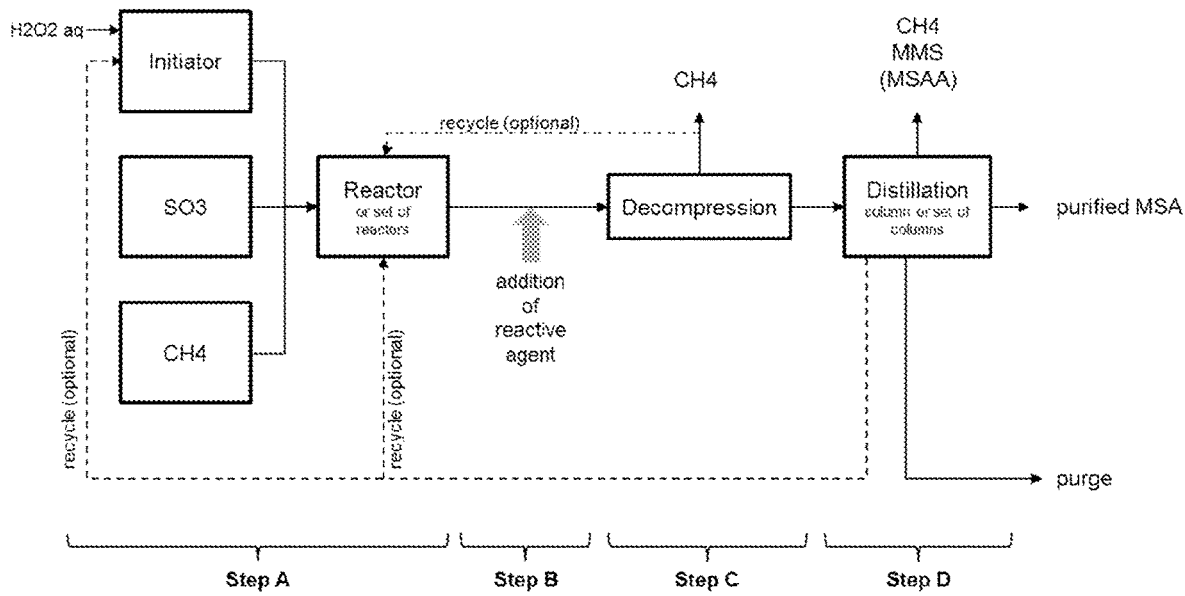
FIG. 1 shows a process set-up including steps A (generation of stream A), B (addition of reactive agent), C (decompression) and D (distillation).
Figure 2:
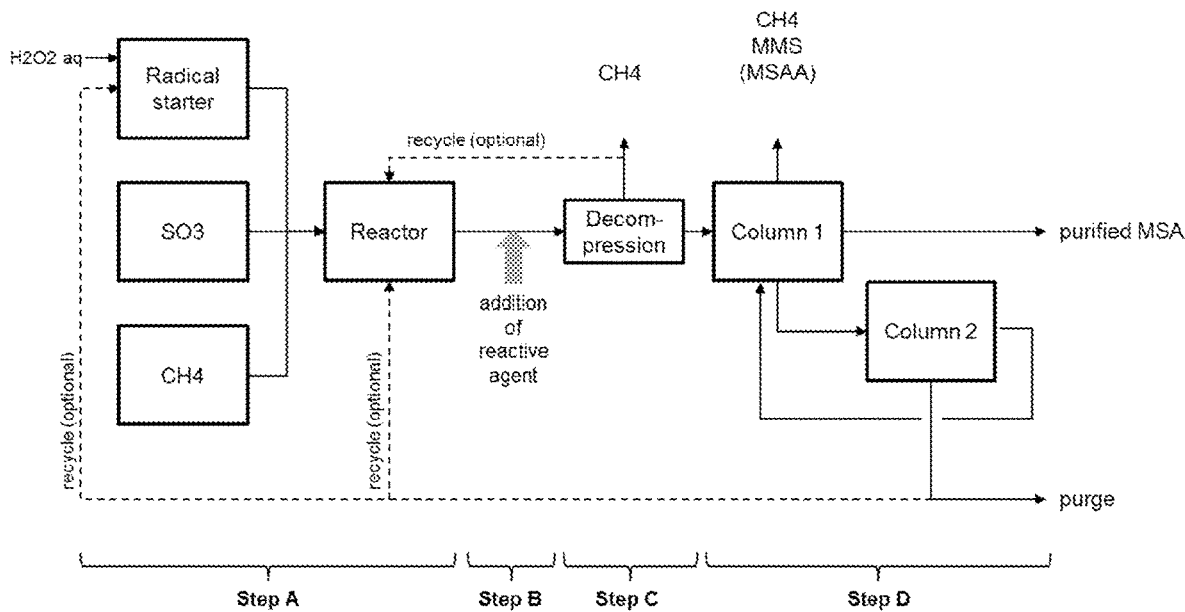
FIG. 2 shows alternative process set-up including steps A (generation of stream A), B (addition of reactive agent), C (decompression) and D (distillation).
Figure 3:
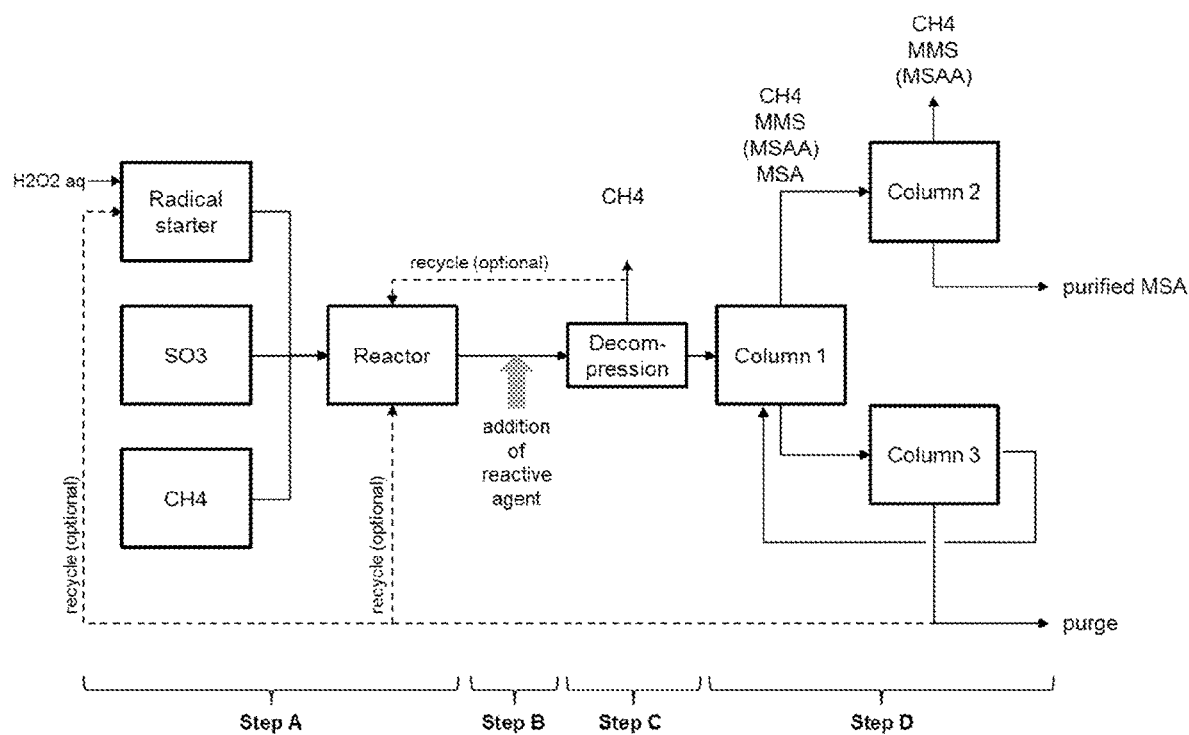
FIG. 3 shows another alternative process set-up including steps A (generation of stream A), B (addition of reactive agent), C (decompression) and D (distillation).

In the following paragraphs, some aspects of the present invention are illustrated by experimental examples.

Example 1: Process According to the Invention with Addition of Water

In step A 352 kg of methane and 1923 kg of $SO_3$ are continuously fed to a reaction system consisting of 3 continuously stirred reactors. The solvent of the reaction is a mixture of sulfuric acid and the reaction product MSA. To minimize losses 498 kg/h sulfuric acid and 213 kg/h MSA are recycled from the bottom part of the distillation in step D back to step A. As initiator 14 kg/h of hydrogen peroxide (70 wt.-%, aqueous solution) are added, which is equivalent to about 0.3 wt.-% $H_2O_2$ in the reaction mixture. The reaction system is operated under a methane pressure of 100 bar and at a temperature of 50° C.

Under these conditions $SO_3$ conversion of 95% is reached. In addition, hydrolysable byproducts are formed. Stream A contains 21.3 wt.-% sulfuric acid, 69.9 wt.-% MSA, 3.2 wt.-% $SO_3$, 5 wt.-% of MSAA and 0.3 wt.-% $CH_4$. The yield of MSA with regard to $SO_3$ is 82% in step A.

In step B, 38 kg/h of water are added, while the system is still pressurized with 100 bar of methane. $SO_3$ and MSAA are converted to sulfuric acid and MSA, respectively.

Then the reaction mixture is depressurized in step C to ambient pressure. The compositions of the liquid and the gas phase in this step are summarized in Table 1.

TABLE 1

Composition in liquid and gas phase after decompression (step C) after the addition of 38 kg/h water in step B

| Component | Liquid Phase | Gas Phase |
| --- | --- | --- |
| H2SO4 | 25 wt.-% | 1 ppm |
| MSA | 75 wt.-% | 40 ppm |
| SO3 | 0 wt.-% | 0 ppm |
| MSAA | 0 wt.-% | 0 ppm |
| CH4 | 0.3 wt.-% | 86.2 wt.-% |
| Mass flow/kg/h | 3024 | 8.9 |

In this case the gas phase contains no $SO_3$ any more. Thus no significant effort for the purification of the methane gas leaving the reactor is needed. One mol of MSAA has completely been converted to two mol of MSA by reaction with water reducing complexity in the distillation since MSA and sulfuric acid are present in the feed to the distillation in step D anyway.

Comparative Example: Process not According to the Invention without Addition of Water In this example stream A has the same mass flow and composition as in Example 1. However, there is no step B, i.e. no addition of water to the pressurized stream A. The composition in the liquid and the gas phase in step C is shown in Table 2.

TABLE 2

Composition of the reaction mixture after decompression (step C) without addition of water

| Component | Liquid Phase/ | Gas Phase |
| --- | --- | --- |
| H2SO4 | 21.3 wt.-% | 1 ppm |
| MSA | 69.9 wt.-% | 36 ppm |
| SO3 | 3.2 wt.-% | 0.14 wt.-% |
| MSAA | 5.2 wt.-% | 14 ppm |
| CH4 | 0.3 wt.-% | 86.2 wt.-% |
| Amount/kg/h | 2995 | 10.34 |

The liquid phase formed in step C is fed to the distillation in step D. The high amount of $SO_3$ remaining in the liquid stream is very likely to cause side reactions at elevated temperatures in the distillation step (formation of methylbisulfite and MSAA).

This makes the distillation and as such the process to obtain anhydrous MSA in high purity more complex.

After decompression the gas phase still contains significant amounts of $SO_3$ that has to be scrubbed to reduce $SO_3$, irrespective if $CH_4$ is flared or burned for energy recovery. In case, it is intended to recycle methane to step A it has to be compressed to 100 bar again. Due to the very high corrosivity of $SO_3$ selection and operation of a suitable compressor is a huge challenge. Although only ppm of MSAA are present in the gas phase a direct recycling might lead to an accumulation of MSAA during extensive recycling of methane.

The invention claimed is:
1. A process to provide anhydrous methanesulfonic acid (MSA) from compositions comprising $SO_3$, comprising
   A) generating a stream A comprising MSA, $SO_3$, and methane under pressure;
   B) adding to stream A under pressure a reactive agent which is capable of reacting with $SO_3$, wherein the reactive agent comprises water, under conditions effective to cause reaction of $SO_3$ with this reactive agent to produce a heavy reaction product having a boiling point higher than the boiling point of MSA, thus generating a stream B;

C) separating stream B to provide a light stream comprising hydrocarbons and a heavy stream comprising MSA and a heavy reaction product having a boiling point higher than the boiling point of MSA; and D) separating the heavy stream by distillation to produce a distillate stream consisting essentially of MSA and a bottoms stream comprising the heavy product.

2. The process according to claim 1, wherein stream A is generated by
 i. producing an initiator for the reaction of SO3 and methane, and
 ii. reacting SO3 and methane in the presence of the initiator generated in the previous step i.

3. The process according to claim 1, wherein the reactive agent not only reacts with SO3, but also hydrolyzes hydrolyzable compounds in stream A.

4. The process according to claim 1, wherein the reactive agent in step B consists of water.

5. The process according to claim 1, wherein the reactive agent is added in stochiometric amounts with regard to SO3 in stream A, or in an overstochiometric amount with regard to SO3 in stream A.

6. The process according to claim 1, wherein the reactive agent is added in stochiometric amounts with regard to the total of SO3 and hydrolysable compounds in stream A.

7. The process according to claim 1, wherein the reactive agent is added in an overstochiometric amount with regard the total of SO3 and hydrolysable compounds in stream A.

8. The process according to claim 1, wherein methanesulfonic acid anhydride (MSAA) is one of the hydrolyzable compounds in stream A.

9. The process according to claim 1, wherein the reactive agent is added to stream A in a static mixer.

10. The process according to claim 1, wherein the reactive agent is added to stream A in a vessel.

11. The process according to claim 1, wherein the reactive agent is added to stream A in a heat exchanger.

12. The process according to claim 2, wherein the initiator is synthesized at temperatures between −5° C. and 50° C.

13. The process according to claim 2, wherein the initiator is synthesized at pressures between 0.8 and 100 bara.

14. The process according to claim 1, wherein stream A is generated in a reactor or a reactor cascade operated at a temperature between 0° C. and 130° C. and a pressure between 20 and 150 bar.

15. The process according to claim 2, wherein part of the bottom stream from the distillation in step D is recycled to synthesize the initiator in step A.

16. The process according to claim 1, wherein part of the bottom stream from the distillation in step D is recycled to the reactor or cascade of reactors in step A.

17. The process according to claim 1, wherein the distillation in step D is operated at temperatures between 130° C. and 220° C. at the bottom of the column or set of columns.

18. The process according to claim 1, wherein the distillation in step D is operated at pressures between 0.1 mbara and 100 mbara at the head of the column or at each individual column in a set of columns.

19. The process according to claim 1, wherein the content of SO3 in the MSA leaving the distillation step D is below 200 ppm.

20. The process according to claim 1, wherein a content of sulfuric acid or equivalents thereof in the MSA leaving the distillation step D is below 500 ppm.

21. The process according to claim 1, wherein the distillation in step D generates anhydrous MSA with a purity of more than 98 wt-% MSA.

22. The process according to claim 1, wherein step C further comprises decompression of steam B, and wherein the decompression of stream B in step C reduces the pressure to 0.5 to 5 bara.

23. The process according to claim 1, wherein step C further comprises decompression of steam B, and wherein the decompression of stream B in step C is done in one step.

24. The process according to claim 1, wherein step C further comprises decompression of steam B, and wherein the decompression of stream B in step C is done in multiple steps (n), wherein the pressure of step n+1 is always lower than the pressure in step n.

25. The process according to claim 1, wherein step C further comprises decompression of steam B, and further comprising heating stream C after decompression, and prior to entering the distillation step D.

26. The process according to claim 20, wherein the sulfuric acid equivalents comprise sulfate.

* * * * *